United States Patent [19]

Starkweather et al.

[11] Patent Number: 5,518,890

[45] Date of Patent: May 21, 1996

[54] METHOD AND APPARATUS FOR THE QUANTITATION AND SEPARATION OF CONTAMINANTS FROM PARTICULATE MATERIALS

[75] Inventors: William H. Starkweather, Gaithersburg; Ronald W. Telford, Pasadena, both of Md.

[73] Assignee: McCormick & Company, Inc., Sparks, Md.

[21] Appl. No.: 979,785

[22] Filed: Nov. 20, 1992

[51] Int. Cl.$^6$ .................. G01N 33/53; G01N 33/553
[52] U.S. Cl. .................. 435/7.94; 435/975; 436/526; 436/531; 436/534; 436/800; 436/808; 530/413; 427/4; 427/212
[58] Field of Search .................. 435/7.9, 7.94, 435/18, 201, 967, 975; 436/518, 526, 531, 532, 533, 534, 800, 806, 808, 810, 827; 530/375, 391.1, 391.3, 396, 413; 427/4, 212

[56] References Cited

U.S. PATENT DOCUMENTS

| | | | |
|---|---|---|---|
| 3,817,837 | 6/1974 | Rubenstein | 435/7.9 |
| 3,966,764 | 6/1976 | Goldenstein et al. | 548/542 |
| 3,987,161 | 10/1976 | Widder | 424/70.1 |
| 4,157,323 | 6/1979 | Yen et al. | 424/497 X |
| 4,177,253 | 12/1979 | Davies et al. | 436/526 X |
| 4,235,973 | 11/1980 | Tschang et al. | 435/188 X |
| 4,452,773 | 6/1984 | Molday | 436/530 X |
| 4,677,067 | 6/1987 | Schwartz et al. | 436/526 X |
| 4,687,732 | 8/1987 | Ward et al. | 435/6 |
| 4,732,811 | 3/1988 | Margel | 428/403 |
| 5,108,933 | 4/1992 | Liberti et al. | 436/501 |
| 5,118,610 | 6/1992 | Kitto et al. | 435/7.21 |
| 5,186,827 | 2/1993 | Liberti et al. | 422/101 X |

FOREIGN PATENT DOCUMENTS 9217786  10/1992  WIPO.

OTHER PUBLICATIONS

*FDA Training Manual for Analytical Entomology in the Food Industry*, Gorham, J. R., Ed., FDA Technical Bulletin No. 2, Food and Drug Administration, Washington, D.C. (1977).

Chamberland et al., "Chitinase–Gold Complex Used to Localize Chitin Ultrastructurally in Tomato Root Cells Infected by *Fusarium Oxysporum* f. sp. Radicislycopersici Compared with a Chitin Specific Gold–Conjugated Lectin," *Histochemical Journal*, vol. 17, pp. 313–321, (1985).

Nargessi et al., "Magnetizable Solid–Phase Fluoro Immunoassay of Human Immunoglobulin G in Serum", *Clinica Chimica Acta*, vol. 111, pp. 65–68, (1981).

Flach et al, *Experientia*, vol. 48, pp. 701–716 (1992).

Dent, R. G., "Extraction of Light Filth From Rice Flours, Extruded Rice Products, and Rice Paper: A Collaborative Study", *J. Assoc. Off. Anal. Chem.* (1982) vol. 65, No. 5, pp. 1086–1088.

Lehninger, Albert L., "Biochemistry", 2nd Edition, Worth Publishers, Inc., New York, (1970), pp. 126–127.

Sigma Chemical Company, "Biochemical and Organic Compounds for Research", 1988 Price List, pp. 726 and 881–882.

Pierce "Immunotechnology Catalog and Handbook", 1990, pp. A–8–A–9.

Molano et al., "An Endochitinase From Wheat Germ", *J. Biol. Chem.*, vol. 254, No. 11, (1979) pp. 4901–4902.

Scrimgeour, K. G., "Chemistry and Control of Enzyme Reactions", Academic Press, New York, (1977), pp. 57–63.

*Primary Examiner*—Toni R. Scheiner
*Assistant Examiner*—Susan C. Wolski
*Attorney, Agent, or Firm*—Oblon, Spivak, McClelland, Maier & Neustadt

[57] ABSTRACT

Contaminants in particulate materials may be separated and quantitated by contacting the particulate material with an immobilized biomolecule which specifically binds to the contaminant, separating the contaminant-immobilized biomolecule complex from the particulate material, and counting the bound contaminant. The method may be conveniently carried out when the biomolecule is immobilized on a magnetic particle. An apparatus for carrying out the method contains a receptacle for receiving a reaction vessel and magnets positioned such that magnetic particles contained in the reaction vessel will be drawn to and adhere to the sides of the reaction vessel when placed in the receptacle.

12 Claims, 3 Drawing Sheets

METHOD AND APPARATUS FOR THE QUANTITATION AND SEPARATION OF CONTAMINANTS FROM PARTICULATE MATERIALS

BACKGROUND OF THE INVENTION

1. Field of the Invention

The present invention relates to a method for the quantitation and separation of contaminants from particulate materials. The present invention also relates to an apparatus and immobilized enzymes and antibodies useful for carrying out such methods.

2. Discussion of the Background

There are a number of industries in which the detection and/or quantitation of contaminants in particulate materials is important. For example, in the food industry the permissible amounts of contaminants, such as insect parts and air (collectively referred to as filth), is closely regulated. Typically, such contaminants are present in the starting materials (ingredients, such as sugar, cocoa, spices, flour, coffee, tea, rice, etc.) used in the preparation of prepared foods, such as baked goods, candies, batters, etc., or packaged for sale to the consumer. In addition, meats, cheeses, and spreads may be contaminated with, in addition to the contaminants described above, microorganisms, such as bacteria, including, e.g., Salmonella, Listeria, Campylobacter, other pathogenic bacteria and a variety of fungi. For the purposes of the present disclosure, the term particulate material includes even those foods and materials not usually thought of as being particulate, such as meats, cheeses, spreads, whole fruits and vegetables, milk and other dairy products, animal feeds, etc., when such foods have been ground, dispersed or pulped, etc.

Although current techniques exist for separating and quantitating such impurities in particulate foods, the existing techniques are characterized as being slow and cumbersome. For example, such methods involve a complex series of steps including various washings with organic solvents and rely ultimately on the floatation of the light filth. Typically, such methods require times on the order of hours, rather than minutes.

In particular, an ELISA assay for insect parts based on the detection of a specific insect muscle protein (myosin) has been reported in *Milling & Baking News*, Apr. 21, 1992, page 29, and in Kitto, *Bulletin, Association of Operative Millers*, March 1991, pp. 5835–5838, and U.S. Pat. No. 5,118,610. However, the laboratory version of this technique requires about 2.5 hours.

In addition, an assay for chitin is disclosed in U.S. Pat. No. 5,118,610. However, this assay relies on the digestion of chitin.

Because the existing techniques for separating and quantitating contaminants in particulate foods are slow, problems arise during the mass production and/or packaging of foods. For example, it may be necessary to shut down a production line while a batch of an ingredient is tested to see if it meets mandated purity standards. Moreover, it may be necessary to discard a batch of prepared and/or packaged food, if an ingredient used in the preparation of the batch is later found to contain an unacceptably high level of contaminants.

Another shortcoming of the existing techniques for separating and quantitating the level of contaminants in particulate foods is that these techniques are characterized as exhibiting a lack of accuracy and reproducibility. Results obtained from such techniques do not correlate well with the actual degree of contamination of the food.

In addition, cosmetics and personal care products, such as creams, powders, toothpastes, etc., may contain many of the same contaminants. Although such cosmetics are not so closely regulated as foodstuffs, this situation may change in the near future. In any event, it is desirable for public health as well as public relations purposes to detect and remove such contaminants from these products. However, the currently available methods for separating and quantitating such contaminants in cosmetics and cosmetic ingredients suffer from the same drawbacks and disadvantages discussed above in the context of foods.

Thus, it would be desirable to provide a method for separating and quantitating contaminants in particulate materials such as foods and cosmetics, etc., which is fast, efficient, and accurate, and gives reproducible and statistically valid results. It would also be desirable to provide an apparatus and reagents which would facilitate the implementation of such a method.

SUMMARY OF THE INVENTION

Accordingly, it is one object of the present invention to provide a fast and efficient method for separating and quantitating contaminants in particulate materials.

It is another object of the present invention to provide an accurate method for separating and quantitating contaminants in particulate materials, which gives reproducible results.

It is another object of the present invention to provide a method for separating and quantitating contaminants in particulate materials, which gives statistically valid results.

It is another object of the present method to provide a fast and efficient method for separating and quantitating filth in particulate foods.

It is another object of the present invention to provide an accurate method for separating and quantitating filth in particulate foods, which gives reproducible results, It is another object of the present invention to provide a method for separating and quantitating filth in particulate foods, which gives statistically valid results.

It is another object of the present invention to provide a fast and efficient method for separating and quantitating insect parts in particulate foods.

It is another object of the present invention to provide an accurate method for separating and quantitating insect parts in foods, which gives reproducible results.

It is another object of the present invention to provide a method for separating and quantitating insect parts in foods, which gives statistically valid results.

It is another object of the present invention to provide a fast and efficient method for separating and quantitating hair in foods.

It is another object of the present invention to provide an accurate method for separating and quantitating hair in foods, which gives reproducible results.

It is another object of the present invention to provide a method for separating and quantitating hair in foods, which gives statistically valid results.

It is another object of the present invention to provide a fast and efficient method for separating and quantitating insect parts in spices.

It is another object of the present invention to provide an accurate method of separating and quantitating insect parts in spices, which gives reproducible results.

It is another object of the present invention to provide a method for separating and quantitating insect parts in spices, which gives statistically valid results.

It is another object of the present invention to provide a fast and efficient method for separating and quantitating microorganisms in spices and foods, such as meats, cheeses and other dairy products, and spreads.

It is another object of the present invention to provide an accurate method for separating and quantitating microorganisms in spices and foods such as meats, cheeses and other dairy products, and spreads, which gives reproducible results.

It is another object of the present invention to provide a method for separating and quantitating microorganisms in spices and foods such as meats, cheeses and other dairy products, and spreads, which gives statistically valid results.

It is another object of the present invention to provide a fast and efficient method for separating and quantitating contaminants in cosmetics.

It is another object of the present invention to provide an accurate method of separating and quantitating contaminants in cosmetics, which gives reproducible results.

It is another object of the present invention to provide a method for separating and quantitating contaminants in cosmetics, which gives statistically valid results.

It is another object of the present invention to provide a novel apparatus for carrying out such methods.

It is another object of the present invention to provide novel forms of immobilized chitinase and other proteins that bind N-acetylglucosamine such as wheat germ agglutinin (WGA) and other lectins and antibodies specific for keratin (anti-keratin) or other ligands that bind to —SH or —S—S— groups for carrying out such methods.

It is another object of the present invention to provide novel forms of chitinase, wheat germ agglutinin, lectins and antikeratin antibodies, which are labelled with a fluorophore, chromogen, or an enzyme useful in an ELISA.

It is another object of the present invention to provide novel kits for carrying out the present method.

These and other objects, which will become apparent during the following detailed description, have been achieved by the inventors' discovery that by: (i) contacting a particulate material with an immobilized biomolecule which binds specifically to the contaminant being assayed to obtain a contaminant-immobilized biomolecule complex: (ii) separating the contaminant-immobilized biomolecule complex and any residual immobilized biomolecule from the particulate material; (iii) and measuring the amount of contaminant bound to the immobilized biomolecule, it is possible to quickly, efficiently and accurately separate and quantitate the contaminant in the particulate material.

The inventors have also discovered that when the biomolecule is immobilized on a magnetic particle the present method may be quickly and efficiently carried out in an apparatus which comprises (a) a receptacle for receiving a reaction vessel and (b) one or more magnets positioned such that magnetic particles contained in the reaction vessel will be drawn to and adhere to the sides of the reaction vessel while the reaction vessel is in the receptacle.

It is also the inventors' discovery that when the contaminant to be separated and quantitated is insect parts that the present method may be quickly, efficiently and accurately carried out by the use of immobilized forms of chitinase or an N-acetylglucosamine-binding lectin. Similarly, when the contaminant to be separated and quantitated is hair, the present method may be quickly, efficiently, and accurately carried out by the use of immobilized anti-keratin or immobilized sulfhydryl (—SH) or disulfide binding reagents.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Thus, in a first embodiment, the present invention provides a method for separating and quantitating contaminants in a particulate material, involving:

(i) contacting the particulate material with an immobilized biomolecule which binds specifically to the contaminant to be quantitated for a time sufficient for any contaminant present in the particulate material to bind to the biomolecule, to obtain a contaminant-immobilized biomolecule complex;

(ii) separating the contaminant-immobilized biomolecule complex and any residual immobilized biomolecule from the particulate material, to obtain a separated fraction; and (iii) counting the amount of contaminant present in the separated fraction.

Suitable particulate materials include foods, such as flour, sugar, spices, and cocoa. In addition, the present method may be applied to foods or materials not ordinarily thought of as being particulate, if a fairly intimate dispersion or suspension may be prepared from the food. Thus the present method may be applied to cheeses and meats, such as beef, pork, lamb, mutton, chicken, duck, turkey, fish, etc., when such foods have been ground. The present method may also be applied to spreads, such as mayonnaise, salad dressings, peanut butter, jams, jellies, etc., when such spreads have been dispersed in a liquid. In addition, the present method may be applied to cosmetics such as powders, creams, toothpastes etc.

Thus, the present method may be applied to materials including, but not limited to:

Beverages and Beverage Materials:

Cocoa, Chocolate, Press Cake, Ground Coffee, Chicory, Hops, Tea;

Dairy Products:

Milk Cheeses, Sour Cream, Cheeses with Seeds and Spices, Spray Dried Milk;

Nuts:

Coconut, Peanut Butter;

Grains and Seeds:

Oats, Wheat, Rice, Flours, Corn Meal, Wheat Germ, Rice Flour, Extruded Rice, Corn Flour, Soy Flour, Wheat Gluten. Starch, Various Baked Goods, Baked Goods with Fruit and Nuts, Breadings, Alimentary Pastes, Pastas, Cereals (all types), Oatmeal, Barley and Infant Cereals;

Egg Products:
  Whole Eggs, Egg Yolks, Egg Whites, Dried Egg Yolks, Dried Egg Whites, Dried Whole Eggs, Dried Egg Whites;
Poultry, Meat, Fish:
  Crab Meat, Fish and Fish Products, Canned Shrimp, Pork Sausage, Ground Beef;
Fruit and Nut Products, Etc.:
  Apple Butter, Apple Chips, Frozen Blackberries, Raspberries, Blueberries, Cherries, FIGS. and Various Fruit Pastes, Jams and Jellies, Citrus and Pineapple Juices, Raisins, Potato Chips, Syrups, Honey Candies;
Vegetables and Vegetable Products:
  Beans and Peas, Canned Broccoli, Canned Corn, Leafy Green Vegetables, Pureed Infant Foods, Mushrooms, Potato Products-Dehydrated, Sauerkraut, Tomato Products-Canned;
Spices and Condiments:
  All Herbs, Whole and Ground,
  All Spices Whole and Ground,
Most condiments
  Peppers, Pepper Sauces, Pickles, Salad Dressings, Horseradish (Prepared), Mustard, Ketchup, Mole, Tamarind Pulp, Gums and Papain.

A key feature of the present method is that the particulate material be contacted with an immobilized biomolecule which binds specifically to the contaminant being analyzed. Thus, the only limitation placed upon the size of the particles in the material to be tested is that the particle size be sufficiently small to permit adequate contact between the immobilized biomolecule and any contaminant present in the material being tested. Thus, for many materials, such as ground spices or herbs and milled grain, no processing of the material is necessary before application of the present method, because the particle size of the material is already sufficiently small to allow good contact between the immobilized biomolecule and the contaminant. However, in the case of materials, such as cinnamon bark, bay leaves, meats, fish, and cheese, it may be preferable to grind the material prior to application of the present method to ensure good contact between the immobilized biomolecule and the contaminant.

Although in principle there is no particular size limitation of the size of the material to be used in the present method, good results have been achieved when the material has an average particle size in which the greatest dimension is less than about 1 cm, preferably less than about 0.5 cm. When detecting the presence of microorganisms in, e.g. meats, it may be preferable to reduce the meat to a suspension of single cells using conventional grinding or digestion techniques.

The present method has been found to give especially good results when the particulate material is a ground spice. Typically, such ground spices will consist of particles having a greatest dimension of less than about 1 cm, preferably less than about 0.5 cm, and accordingly, these materials need not be further processed before application of the present method.

Examples of contaminants present in such particulate materials include filth, such as whole insects, insect parts, and hair, as well as microorganisms, such as Salmonella, Listeria, Camphylobacter and other microbial pathogens including a variety of fungi. In the case of particulate foods such as flour, spices, cocoa, sugar, etc., the occurrence of light filth such as hair and insect parts is a particular problem, and the separation and quantification of such light filth in such particulate foods represents a preferred embodiment of the present method. In the case of spices, meats, cheeses, and spreads, the occurrence of microbial contaminants is a noteworthy problem, and the separation and quantification of such microbial contaminants from such foods represents another preferred embodiment of the present method.

The choice of the exact immobilized biomolecule will depend on the nature of the contaminant to be separated and quantitated. In general, the biomolecule should bind the contaminant with a $K_d$ of at least about $10^6$, preferably at least about $10^7$–$10^9$.

When the contaminant being assayed is insect parts, the biomolecule may suitably be chitinase, wheat germ agglutinin, or any other lectin which specifically binds with N-acetylglucosamine, such as *Bandeiraea simplicifolia* BS-II, *Datura stramonium, Lycopersicon esculentum, Phytolacca americana, Solanum tuberosum,* and *Ulex europaeus* UEA II. Wheat germ agglutinin (*Triticum vulgaris* lectin) and the other listed lectins are all commercially available from, e.g., Sigma Chemical Company of St. Louis, Mo. The preferred biomolecule is chitinase. Chitinase (also referred to as chitodextrinase; poly[1,4-β-(2-actamido-2-deoxy-D-glucoside)]glycanohydrolase; and EC 3.2.1.14) is a well known enzyme which is commercially available from, e.g., Sigma Chemical Company, CalBiochem Corp. and Boehringer Mannheim Corp. Other commercial sources may exist in Pacific Rim nations or in developing countries. Depending on the biological source, chitinase binds to chitin with a $K_d$ of about $10^7$–$10^{12}$. The inventors have discovered that chitinase also binds tenaciously to whole insects and insect parts.

When the contaminant to be assayed is hair, the biomolecule may be an antibody which binds specifically to keratin. Alternatively, the biomolecule may be any compound which reacts selectively with sulfhydryl or disulfide groups, such as those disclosed in the *Pierce Immunotechnology Catalog and Handbook* and discussed in the context of crosslinking below. The preferred bimolecule is an antibody which binds specifically to keratin, anti-keratin. For the purposes of the present method, either polyclonal or monoclonal antibodies may be used. Polyclonal reagents may be used if the $K_d$ is greater than $10^7$ which is usual for non affinity purified polyclonal antibodies. Polyclonal antibodies also recognize many more epitopes than do monoclonal antibodies which by definition recognize a single epitope. Further, since keratin is a highly conserved protein, it is possible to use one polyvalent anti-keratin for the detection of hair from a number of species, such as human hair, rodent hair (including rat hair), dog hair, horse hair, cat hair, etc. Anti-keratin is known to bind to keratin with a high $K_d$, and anti-keratin also binds whole hair tenaciously. Anti-keratin K 4252 is commercially available from numerous biotechnology companies such as DAKO, Zymed, Sigma etc. and also may be obtained from non-commercial sources such as Universities in North America and the European Community. Alternatively, if it is desired to detect only a specific type of hair, such as rodent hair, particularly rat or mouse hair, then the use of a monoclonal antibody which specifically binds the specific hair to be detected is preferred.

In the case of a microbial contaminant, the biomolecule is suitably any antibody which binds to the surface of the microbe. For example, when the contaminant being assayed is salmonella, the biomolecule can be an antibody which binds specifically to Salmonella.

The biomolecule used in the present assay may be immobilized by any conventional technique. Typically, conventional immobilization techniques involve the use of a bifunctional crosslinking reagent, which contains a first functional group which reacts with a group on the biomolecule to be immobilized and a second functional group which reacts with a group on the substrate on which the biomolecule is to be immobilized. The two functional groups on the bifunctional crosslinking reagent may be the same, as in the case of glutaraldehyde, $OCH(CH_2)_3CHO$. Alternatively, the two functional groups on the crosslinking reagent may be different, as in heterobifunctional crosslinking reagents. A great number of bifunctional crosslinking reagents are known, and a list of such agents is provided in the *Pierce Immunotechnology Catalog and Handbook*, Pierce, Rockford, Ill., 1990, which is incorporated herein by reference. Additional examples of crosslinking agents are provided in U.S. Pat. Nos. 3,817,837, 3,966,764, and 4,687,732, which are incorporated herein by reference. The exact procedures, such as reaction temperature and incubation time, for immobilizing the biomolecule on the support are well within the abilities of one skilled in the art.

Chitinase is known to contain free amino and sulfhydryl groups readily accessible to crosslinking reagents. Thus, it is possible to immobilize chitinase by using a bifunctional crosslinking reagent which contains at least one group which will react with either the accessible amino or sulfhydryl groups on chitinase to form a stable covalent linkage. Such groups include, for example, aldehyde groups. Alternatively, the substrate may already contain carbonyl groups on its surface, which may react directly with the accessible amino and/or sulfhydryl groups on chitinase. Good results have been obtained when chitinase has been immobilized on a substrate having exposed carbonyl groups.

Antibodies are known to contain sugar groups which may be oxidized to contain carbonyl groups with, e.g., periodate. These carbonyl groups may then be reacted with a crosslinking agent which contains, e.g., an $H_2N—$ group.

The choice of substrate on which the biomolecule is to be immobilized will, in part, depend on the method to be used to separate the contaminant-immobilized biomolecule complex and any residual immobilized biomolecule from the particulate material. If, for example, simple physical or mechanical separation is to be employed, then the biomolecule may be immobilized on any support which can be conveniently separated from the particulate material by such methods. Examples of such supports include glass beads, plastic beads, glass rods, plastic rods, glass slides, plastic slides, glass tubes, plastic tubes, etc. Alternatively, if the separation method will rely on the use of a magnet, then the biomolecule is preferably immobilized on a magnetic support, such as magnetic particles. Good results have been obtained when magnetic particles having free carbonyl groups on the surface are used as the substrate for immobilizing biomolecules having accessible amino and/or sulfhydryl groups, such as chitinase.

No particular size limitation is imposed on the support on which the biomolecule is immobilized. When using magnetic beads as the support, a suitable size is an average particle diameter of 1 to 10 micrometers. Magnetic beads having an average particle diameter of 2 to 5 micrometers are preferred.

As noted above, the contacting of the particulate material with the immobilized biomolecule must be carried out in a manner such that there is adequate contact between the immobilized biomolecule and any contaminant, in the sample being tested, to form a contaminant-immobilized biomolecule complex. Typically, such contacting will be carried out when the particulate material and the immobilized biomolecule are present in an aqueous suspension. The aqueous phase of the solution may contain additional ingredients, such as detergents, surfactants, $C_{1-10}$-alcohols, salts (NaCl, KCl, etc.), antifoaming agents, etc. Further, the aqueous phase may be buffered to maintain a pH at which the biomolecule retains its activity.

The aqueous suspension containing the particulate material and immobilized biomolecule may be prepared by a variety of techniques, and, there is no constraint on the order of addition of the various components. Thus, a suspension of the particulate material may be prepared first and then the immobilized biomolecule added, or a suspension of the immobilized biomolecule may be prepared first and then the particulate material added. Alternatively, the particulate material may be mixed or placed in a reaction vessel with the immobilized biomolecule first and then the aqueous phase added. Further, additional components or ingredients may be added after the initial mixing and during the contacting step. In the case of ground spices, good results have been obtained when the ground spice is first mixed with the aqueous phase and then the immobilized biomolecule is added.

When mixing the particulate material with the aqueous phase it is preferred to utilized stirring to achieve adequate mixing. In addition, when the particulate material is a ground spice, the use of sonication has been found to afford good results. Any conventional ultrasound apparatus may be used. Good results have been obtained using a TEKMAR Model No. 375. Suitably, the aqueous suspension of particulate material is sonicated for a time of 1 to 5 minutes, preferably 3 minutes, at a power of 50 to 100%, preferably 50%. It is also possible to achieve good results using conventional microwave heat and/or vigorous stirring, without sonication.

After the aqueous suspension of the particulate material has been formed, the immobilized biomolecule is added. There is no particular time limitation on the contacting step. It is only necessary that the contacting step be carried out for a time sufficient for the formation of the contaminant-immobilized biomolecule complex. Suitably, the contacting step is carried out for a time of 5 to 30 minutes, preferably about 15 minutes. In the interest of efficiency, it is preferred to utilize a shorter time, if possible.

The contacting step is suitably carried out in a reaction vessel. No particular material or size limitations are imposed on the reaction vessel, so long as the reaction vessel is compatible with the components of the reaction mixture and is sufficiently large to accommodate the reaction mixture. Good results have been achieved by using tubes, such as 50 ml plastic centrifuge tubes. When using an apparatus which contains a reservoir for receiving material from the bottom of reaction vessel, it may be preferable to use a reaction vessel which either (1) contains means for releasing material from the bottom such as a stopcock or valve or (2) can be opened from the bottom by, for example, a puncturing means.

After completion of the contacting step, the contaminant-immobilized biomolecule complex and any residual immobilized biomolecule is separated from the particulate material or aqueous suspension of the particulate material. The separating step may be carried out in a variety of ways. First, the separating step may be accomplished by simple mechanical means. For example, if the biomolecule is immobilized on a support such as a slide or rod, the support may be removed from the suspension by hand. Further, if the biomolecule is immobilized on a support such as a bead which has a different average particle size than that of the particulate material, the support may be separated by means of a selective filter or sieve. For example, if the support is larger than the particulate material, passing the reaction mixture through a sieve fine enough to trap the support, but not the particulate material, will effect the separation. If the support is smaller than the particulate material and the contacting step is carried out in an aqueous suspension, then it may be necessary to use two sieves or filters, one to separate the particulate material from the support and another to separate the support from the aqueous phase.

It is preferred that the separating method employ a magnet. In this case, the support will, of course, contain a material which will be attracted to a magnet. It is preferred that the support be magnetic itself. A magnet may be employed in the separating step in a number of ways. In its simplest application, the magnet may be inserted into the reaction mixture containing the particulate material and immobilized biomolecule after completion of the contacting step. In this way, the contaminant-immobilized biomolecule complex and any residual immobilized biomolecule may be separated from the particulate material by simply withdrawing the magnet after the magnetic support has been drawn to and adhered to the magnet. In such a method it may be preferable to utilize a magnet which is coated either with glass or a plastic, such as polyethylene, polypropylene, nylon, etc, to facilitate the efficient separation of the support from the particulate material.

In a preferred embodiment, a magnet is positioned outside the reaction vessel and close enough to the reaction vessel Such that the magnetic support is drawn to and adheres to a side of the reaction vessel, and the aqueous suspension of the particulate material is then removed from the reaction vessel. This removal may be carried out by a number of methods, including pipetting, etc. However, it is also possible that the removal of the aqueous suspension of the particulate material be carried out by draining the suspension from the bottom of the reaction vessel. It is preferred that four magnets are employed, rather than one.

When using more than one magnet, it is preferred that the magnets be arranged such that they are evenly spaced about the reaction vessel. Thus, when using two magnets, the south pole to north pole vectors of the two magnets are preferably parallel and lines connecting opposite poles of the two magnets are substantially perpendicular to the south pole-north pole vectors of the magnets. Further, when using more than two magnets, the magnets are arranged such that the vector from the south pole to the north pole for each magnet is colinear with and centered on a side of a regular polygon in which the number of sides equals the number of magnets. Thus, when three magnets are used, the south pole-north pole vector for each magnet will be colinear with and centered on a different side of a equilateral triangle. When four magnets are used, the south pole-north pole vector for each magnet will be colinear with and centered on a different side of a square.

It is further preferred that the magnets be arranged such that direction of the south pole-north pole vector for each magnet alternates. Thus, for any pair of nearest neighbor magnets, the poles of the two magnets which are closest to one another will either both be north or both be south.

It may be preferred to wash the separated fraction containing the contaminant-immobilized biomolecule complex and any residual immobilized biomolecule after the separating step to insure that the separated fraction is substantially free of particulate material and any contaminants other than those bound to the immobilized biomolecule. This washing may be accomplished with water which contains, for example, a buffer.

After the contaminant-immobilized biomolecule complex and any residual immobilized biomolecule have been separated from the particulate material, the amount of contaminant bound to the immobilized biomolecule is then determined. This counting step may be carried out in a number of ways. For example, if the contaminant is macroscopic, it may be counted by visual inspection by the naked eye. Smaller contaminants may be counted visually with the aid of a magnification device such as a microscope.

In some cases, it may be preferable to visualize the contaminant in the counting step by means of a colorimetric procedure. In such a procedure the visualization of the contaminant is enhanced. Such colorimetric visualization enhancement may be carried out by a number of methods. For example, the separated fraction, which contains the contaminant-immobilized biomolecule complex and any residual immobilized biomolecule, may be treated with a chromophore, dye, or fluorophore which is covalently linked to the same biomolecule immobilized on the support or a different biomolecule which also binds specifically to the contaminant being assayed. In this way, the contaminant, bound to the immobilized biomolecule, will also be bound to another biomolecule which is in turn linked to a chromophore, dye or fluorophore. This type of procedure is similar in concept to a sandwich assay. For example, a fraction containing immobilized chitinase and insect part-immobilized chitinase complex may be treated with either (a) chitinase, which is linked to a fluorophore, chromogen or ELISA enzyme, or (b) an N-acetylglucosamine-binding lectin labelled with a fluorophore, chromogen or ELISA enzyme. Alternately, if the immobilized biomolecule is an N-acetylglucosamine-binding lectin, then the visualization enhancement may utilize either labelled chitinase or labelled lectin.

The types of biomolecules suitable for use as the biomolecule bound to the chromophore are the same as those described above in the context of the immobilized biomolecule, and the same types of crosslinking reagents as described above may be used for binding the biomolecule to the chromophore, dye, or fluorophore. The exact conditions, such as reaction temperature and incubation time, for binding the biomolecule to the chromophore are well within the abilities of one skilled in the art. Suitable chromophores, dyes, and fluorophores include basic dyes such as pararosaniline, new fuchsin, safranin O, methyl green, azure B, Romanowski stains and fluorophores such as fluorescein isothiocyanate, tetramethylrhodamine isothiocyanate, calcflor 40, Texas red and various coumarin derivatives. These are examples, and the method is not limited to these alone, but should include all dyes and fluorophores that can be covalently coupled to the biomolecule via the active functional group contained on the indicator molecule.

Alternatively, the colorimetric visualization enhancement may be carried out by treating the separated fraction with another biomolecule, which specifically binds to the contaminant and which is linked to an enzyme suitable for use in an ELISA. Enzymes suitable for use in an ELISA and the procedures involved in carrying out as ELISA are described in Tjissen, P., "Practice and Theory of Enzyme Immunoassays", in: *Laboratory Techniques in Biochemistry and Molecular Biology*, RH Burdon and PH Van Knippenberg (Eds) Vol. 15, Elsevier, Amsterdam, 1985, which is incorporated herein by reference.

In the case of chitinase, good results have been achieved by linking chitinase to fluorescein isothiocyanate (FITC), CASCADE BLUE™ and calf-intestine alkaline phosphatase. Other suitable reagents for visualization enhancement include chitinase/beta-galactosidase, chitinase/beta-glucuronidase, chitinase/horseradish peroxidase, chitinase/esterase, chitinase/4-aminobutyl N-ethyl isoluminol and a 3-layer magnetic bead/chitinase/enzyme conjugate. The latter consists of magnetic beads linked to chitinase and any one of the above mentioned enzymes (or dyes or fluorophore) covalently linked to chitinase. Thus, incubation of food products with this material followed by magnetic extraction would allow direct quantitation of contaminants without requiring a second incubation with chitinase labeled with an indicator molecule.

When the contaminant being assayed is able to absorb or bind a chromophore, dye or fluorophore directly, it is possible to achieve the visualization enhancement by a treatment with a chromophore, dye or fluorophore which is not bound to a biomolecule which specifically binds the contaminant. For example, when the contaminant is a microbe, such as salmonella, the visualization enhancement may be achieved by treating the salmonella with a chromophore, dye or fluorophore which is taken up by the microbe. Examples of chromophores, dyes, and fluorophores which are taken up by microbes include Gram stain, Silver stains, acid fast stains, Wright and Giemsa stains and other well known microbiologic chromophores. The treatment of the microbes with the chromophore, dye, or fluorophore may take place either before, during or after either the contacting step or separating step; in other words, anytime before the counting step.

As noted above, the counting step may be carried out by direct visual inspection. However, it is preferred that the counting step be carried out by means of an automated counter. When using an automated counter, it is preferred that the visualization of the contaminant be enhanced with a chromophore, dye, or fluorophore as described above. A suitable counting system consisting of an Olympus VANOX microscope, an automated stage supplied by Robbins Scientific, a color video camera attached to the microscope, a frame grabber and software supplied by RM Biometrics have provided acceptable results. Other software programs may be available and microscope systems as supplied by Zeiss, Nikon, Wild and Leitz are suitable.

The inventors have discovered that the present method is both a quick and efficient way to separate and quantitate contaminants in a particulate material. As described in the Examples given below, the present method can reduce the time required for quantitating insect parts in a ground spice from hours to minutes. The present method has further been found to be both precise and accurate. As also described below, the present method yields values for the amount of insect parts in ground spice which correlate well with the actual degree of contamination.

Another advantage of the present method, when applied to detecting insects and insect parts, is that this method is useful for detecting insects at all stages of development. Thus, since insects contain large amounts of chitin in all stages of development, the present method is useful for detecting insect eggs, larva, and pupa, in addition to whole adult insects and insect parts.

In another embodiment, the present invention provides an apparatus for carrying out the present method. As noted above, the apparatus comprises a receptacle for receiving a reaction vessel. No particular size limitation is placed on the receptacle, so long as the receptacle is large enough to receive the reaction vessel and small enough to permit the reaction vessel to be positioned sufficiently close to the magnet(s).

The apparatus also comprises at least one magnet positioned such that any magnetic particles in a reaction vessel will be drawn to and adhere to the side of the reaction vessel when it is in the receptacle. Preferably, the magnet(s) is a super neodymium-iron boron magnet. Particularly, preferably, steel plates are placed over the south pole and north pole faces of the magnet(s).

The apparatus may also comprise a reservoir for receiving material from the bottom of the reaction vessel when the reaction vessel is in the receptacle. When the reaction vessel is made of a material which may be punctured, the apparatus may preferably comprise a means for puncturing the reaction vessel when it is in the receptacle. Such means may be, for example, a pin which may be manually or automatically activated to puncture the bottom of the reaction vessel.

In further embodiments, the present invention relates to immobilized chitinase, immobilized N-acetylglucosamine-binding lectin (in particular wheat germ agglutinin), immobilized ligands which specifically bind —SH or —S—S— groups, and immobilized anti-keratin. As noted above, the immobilized chitinase and anti-keratin are preferably immobilized on magnetic particles. Especially good results have been obtained by immobilizing chitinase on acrolein-treated magnetic particles obtained from CORTEX, INC. These particles have a size range of 1–10 micrometers with an average size of 5 micrometers. The surface of these beads contains numerous $HC=O$ functional groups that readily react with free $—NH_2$ residues available on the chitinase molecule.

Figure 1A:
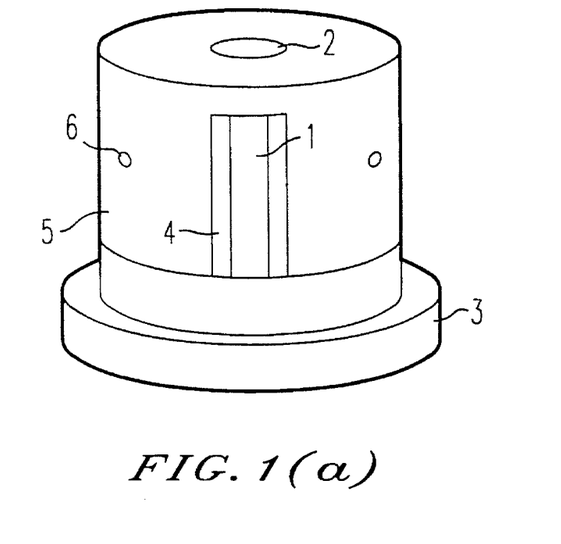
FIGS. 1a and b illustrate two views of one embodiment of an apparatus for carrying out the present method.
Figure 1B:
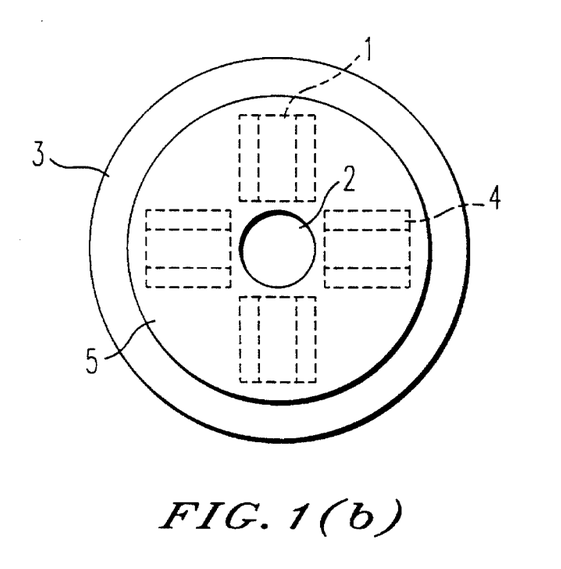

Referring now to the drawings, wherein like reference numerals designate identical or corresponding parts throughout the several views, and more particularly to FIG. 1a thereof, which shows a side view of one embodiment of the present apparatus, it is seen that a preferred embodiment of the apparatus has magnets (1) disposed along the sides of a cylindrical receptacle (2). The pole faces of the magnets (1) are covered with steel plates (4) and the magnets are housed in a housing (5). The housing is fastened to the base (3) by screws (6). FIG. 1b shows a top view of this embodiment and reveals four magnets (1) disposed regularly about a receptacle (2). In this embodiment, the receptacle (2) is about 1⅛ inches in diameter, and the magnets (1) are about 1 inch in length. The outer diameter of the apparatus is about 4¼ inches.

Figure 2A:
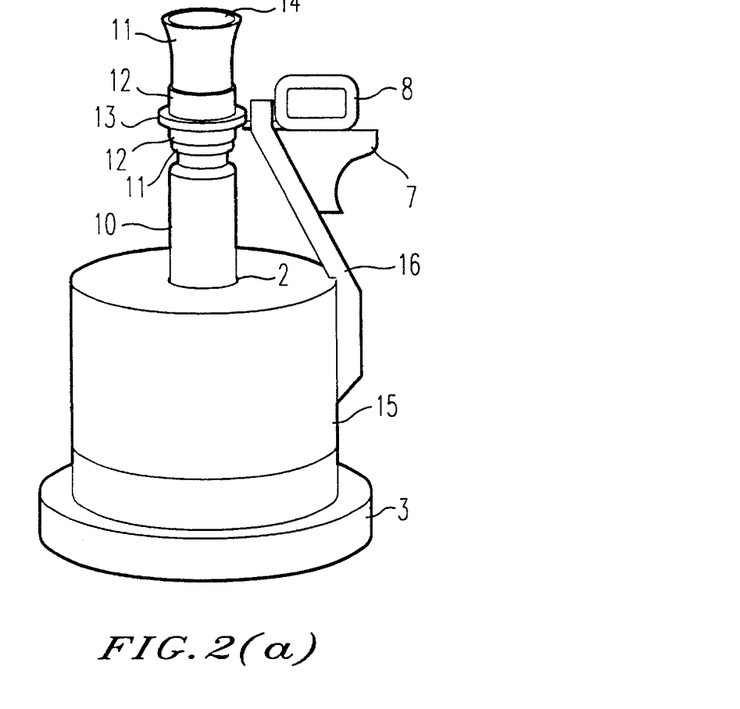
FIGS. 2a and b illustrate two views of the apparatus shown in FIG. 1 with sleeve in place.
Figure 2B:
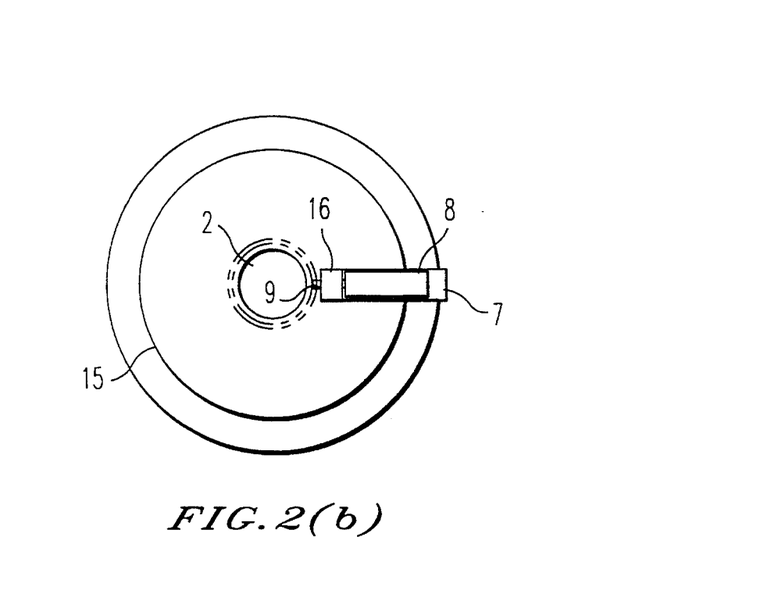

FIG. 2a shows a top view of the same apparatus with the metal sleeve (15) in place over the housing (5). An armature (16) is connected to the sleeve (15) and a base (7) is connected to the armature (16). A ring (8) rests on the base (7) and is connected to a pin (9). The ring (8) may be moved along the base (7) such that the pin (9) either protrudes or does not protrude from the top portion of the armature (16). As depicted, the pin (9) is protruding from the armature. By these means it is possible to provide support for a tube reaction vessel (10) when present in the receptacle. As shown, the rubber sleeve (11) is placed over the top of the tube reaction vessel (10) and a metal sleeve (12) and metal ring (13) are placed over the rubber sleeve (11). The metal ring (13) rests against the pin (9) for support. In this way, a removal device, such as a pipette (not shown) may be inserted into the reaction vessel (10) via the opening at the top of the rubber sleeve (14) without the risk of disturbing the tube reaction vessel and dislodging magnetic particles adhered to the sides of the tube reaction vessel (10).

Figure 3A:
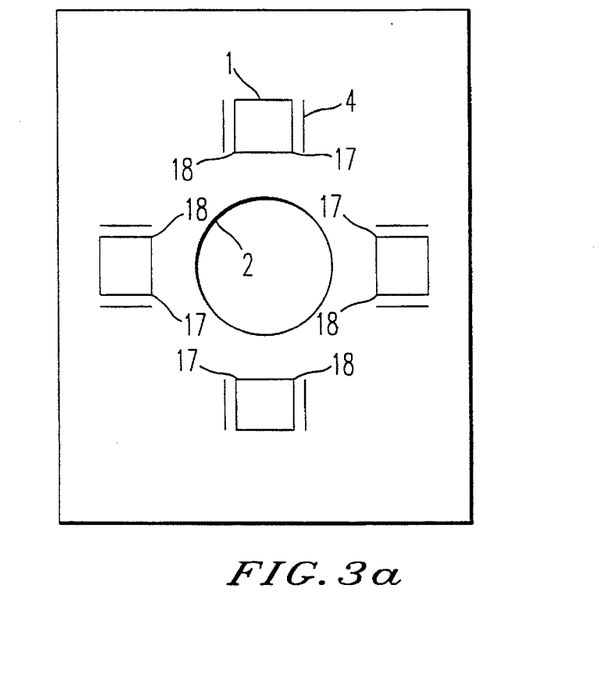
FIGS. 3a and b show preferred arrangements of magnets in two embodiments of the present invention.
Figure 3B:
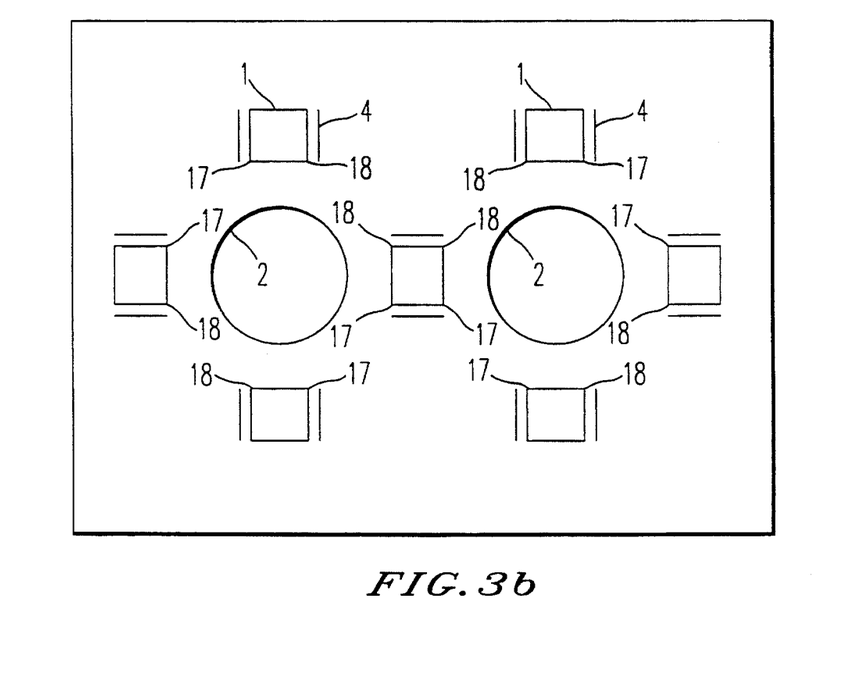

FIGS. 3a and b illustrate preferred arrangements of the magnets (1). In FIG. 3a, four magnets (1) surround the receptacle (2), while in FIG. 3b, seven magnets (1) are used to surround two receptacles (2). The idea of using one magnet (1) to service more than one receptacle may be extended to apparatus containing more than two receptacles (2). Also shown in FIGS. 3a and b is the steel plates (4) on the north pole and south pole faces of the magnets. In addition, the relative arrangement of the north pole face (17) and the south pole face (18) of adjacent magnets is shown.

In another embodiment, the present invention relates to kits for carrying out the present method. In its simplest form the present kit may comprise a first container means comprising an immobilized biomolecule which binds specifically to the contaminant to be quantitated. Preferably, the biomolecule will be immobilized on magnetic beads. Preferably, the biomolecule is chitinase, wheat germ agglutinin, or antikeratin. In some embodiments, it may be desirable to include a second container means in the kit, wherein said second container means comprises a visualization enhancement agent, such as a chromogen, fluorophore, or ELISA enzyme covalently linked to either the same or a different biomolecule which specifically binds to the contaminant being assayed. Thus, the second container means may contain, for example, chitinase, wheat germ agglutinin, or antikeratin which have been labeled with a chromogen, fluorophore, or ELISA enzyme.

In yet another embodiment, the present kit may comprise a third container means which comprises a calibration sample which contains a sample containing a predetermined amount of contaminant. For example, the third container means may contain a preweighed material, such as a ground spice, sugar, cocoa, flour, coffee, tea, etc. which contains or to which has been added a known quantity of contaminant.

Of course, the first, second, or third container means referred to above may be any conventional container means such as a sealed vial, screw cap jar or bottle, sealed foil or plastic package, etc.

It may also be preferable to include in the present kit a carrier which is compartmentalized to receive one or more container means, such as the first, second, or third container means described above, in close confinement. The carrier may be any conventional carrier, such as a cardboard box, plastic or styrofoam container, so long as it receives the first, second, or third container means in close confinement therein. In addition, it may be preferable to include in the present kit written information or instructions useful for carrying out the present method. For example such written information or instructions could include: a) the amount of immobilized biomolecule contained the first container means, including the total amount or activity of the biomolecule; b) the amount of the visualization enhancement agent contained in the second container; c) the amount of the contaminant contained in the third container; and d) a recipe for carrying out the present method. Of course, the written information or instructions may be provided on separate sheets or on any of the first, second, or third container means.

Other features of the invention will become apparent in the course of the following descriptions of exemplary embodiments which are given for illustration of the invention and are not intended to be limiting thereof.

EXAMPLES

A. MAGNETIC BEADS:

Three different bead configurations, 1 micron, 10 micron and a colloidal suspension, have been explored with respect to insect fragment acquisition and image capture capability using BioQuant image analysis software. The large particles interfere with frame grabbing and the colloidal particles require an extended exposure to supermagnets for complete extraction. The 1 micron particles display a uniform size distribution, are rapidly captured in a magnetic field and do not interfere with image analysis. An amine activated version and an aldehyde activated version of the of the 1 micron iron beads has been employed for the research described in the subsequent sections of this report.

B. PRODUCTION OF MAGNETIC BEADS COVALENTLY COUPLED TO CHITINASE:

Chitin, a N-acetylglucosamine polysaccharide is a principle component of the exoskeleton of insects. Microbial chitinase binds avidly to chitin ($K_d=10^7-10^{12}$) resulting in degradation of the polymer to N-acetylglucosamine and lower molecular weight chitin breakdown products. The high avidity of this enzyme for substrate suggested that chitinase coupled to magnetic particles might be useful for extracting insect fragments from spice solutions. Chitinase contains free amino and sulfhydryl groups readily accessible to protein modification reagents. Magnetic particles must be modified to present similar reactive sites. Amine activated 1-micron iron particles, available commercially from CORTEX, INC. were activated with glutaraldehyde. This procedure consisted of washing 2 g of beads 5 times in deionized water then incubating overnight in 40 mL of a 1% v/v glutaraldehyde solution. The beads were then washed in water followed by 3 washes in a carbonate/acetate buffer, pH 8.5. The beads were suspended in 20 mL of this buffer after the final wash. Chitinase, 30 mg was dissolved in 4 mL of carbonate acetate buffer, added to the beads and incubated with gentle rocking for 2 hours. After 2 hours the beads were washed 4 times in 1 mol/L NaCl and then incubated for 1 hour in a 1 mol/L glycine/NaOH solution to block remaining aldehyde functional groups. The beads were then washed thoroughly in water followed by 3 washes in a bis tris maleic acid buffer, pH 6.2. After the final wash the beads were suspended in a 150 mmol/L bis tris buffer, pH 6.2 containing 1% hydroxypropyl-beta-cyclodextrin and 0.16% N-acetylcysteine.

Acrolein coated beads with an average diameter of 2 micrometers were obtained from CORTEX, Inc. These beads contain an active surface aldehyde functional group and do not require preactivation if the molecule to be coupled contains free —$NH_2$ groups. On gram of beads were washed thoroughly in deionized water and 3 times in a 200 mmol/L bicarbonate buffer, pH 9.2. After the final wash, the beads were suspended in 7 mL of bicarbonate buffer. Chitinase, 8–40 mg, was dissolved in 3 mL of bicarbonate buffer, added to the beads, and the suspension was incubated with gentle mixing for 2 hours. After 2 hours the beads were washed thoroughly in bicarbonate buffer, and incubated for 1 hour in bicarbonate buffer containing 1 mol/L glycine. The suspension was then washed thoroughly in 100 mmol/L acetate buffer, pH 4.0 and finally 3 times in 150 mmol/l bis-tris buffer, pH 6.2. After the final wash, the beads were suspended in the bis tris buffer containing 1% hydroxypropyl-beta-cyclodextrin and 0.16% N-acetylcysteine.

Amine activated beads obtained from CORTEX, INC. were also coupled to chitinase using a heterobifunctional agent maleimidobenzoyl-N-hydroxysuccinimide ester (MBS). One gram of beads was washed thoroughly in water then 3 times in a 150 mmol/l phosphate buffer, pH 6.8. After the final wash, the beads were suspended in 10 mL of phosphate buffer to which was added 25 mg of MBS dissolved in 1 mL of dimethylsulfoxide. The maleimido tail reacts rapidly with amine groups so a 15 minute incubation was used. After 15 minutes, the beads were washed once in 50 mL phosphate buffer and resuspended in 10 mL of the same buffer. Chitinase, 15 mg was dissolved in 2 mL of phosphate buffer, added to the beads and incubated for 1 hour with gentle mixing. The beads were washed twice in phosphate buffer, then incubated in 20 mL of phosphate buffer containing 150 mmol/L N-acetylcysteine to block unreacted succinimido residues. The beads were then washed with bis-tris as described previously and stored in 50 mL of bis tris buffer containing 1% hydroxypropyl-beta-cyclodextrin and 0.16% N-acetylcysteine.

To determine the ability of these different preparations to react with insect chitin, insect fragments were weighed out in 2 mg aliquots, placed in tubes and suspended in 20 mL of 150 mmol/L bis tris buffer, pH 6.2. Volumes of beads ranging from 25–500 microliters were added and incubations carried out from 5–45 minutes. The suspensions were then placed in the magnetic device described in this application for 5 minutes. After 5 minutes the supernatant fluid was removed by pipet and examined for insect fragments. The results suggested that acrolein activated beads were most efficient in recovering fragments. Fifty microliters of this product removed greater than 90% of contaminants in 15 minutes while 200 microliters of glutaraldehyde coupled amine activated beads required 30 minutes for comparable recovery. An equivalent volume of MBS coupled beads required 15 minutes incubation.

C. PRODUCTION OF CHITINASE LABELED WITH REPORTER MOLECULES:

Chitinase has been covalently coupled to fluorescein isothiocyanate (FITC), CASCADE BLUE™ and calf intestine alkaline phosphatase. The methods employed are as follows:

FITC: To 8 mg of chitinase dissolved in 3 mL of 200 mmol/l carbonate/acetate buffer, pH 8.5, was added 8 mg of FITC dissolved in 2 mL of the same buffer. The solution was allowed to stand 4 hours with gentle mixing. It was then dialyzed overnight against 4 liters of 150 mmol/L bis-tris buffer, pH 6.2, containing 0.16% N-acetylcysteine. The next morning, the conjugate was removed and hydroxypropyl-beta-cyclodextrin added to a final concentration of 1%.

CASCADE BLUE™: The procedure used to conjugate CASCADE BLUE™ to chitinase is identical to that for FITC.

ALKALINE PHOSPHATASE: The procedure for covalently linking alkaline phosphatase to chitinase with glutaraldehyde is a modification of the 1-step procedure described by Tjissen. To 8 mg chitinase dissolved in 4 mL of 200 mmol/L carbonate/acetate buffer, pH 8.5, was added 16 mg of calf intestine alkaline phosphatase (BIOZYME, Inc.-An enzyme of comparable purity can be obtained from Sigma chemical, Boehringer Mannheim Corp., Worthington, Inc., and others).

To this was added 200 microliters of 1% glutaraldehyde. This solution was incubated for 3 hours with gentle mixing. After 3 hours, 200 microliters of a 2 mol/L lysine solution was added to block remaining aldehyde groups. The solution was then dialyzed against 2 changes of 150 mmol/L bis-tris buffer, pH 6.2, containing $1 \times 10^{-3}$ mol/L magnesium acetate and $1 \times 10^{-4}$ mol/L zinc acetate. The dialysis was for 48 hours at 2°–8° C. After 48 hours, the material was removed from dialysis. Hydroxypropyl-beta-cyclodextrin was added to a concentration of 1% and protease free bovine serum albumin added to a concentration of 2%.

FITC and CASCADE BLUE™ labeled conjugates are visualized by well documented fluorescent microscopy techniques. Alkaline phosphatase labeled reported reagents can be localized using 5-bromo-4-chloro-3-indolyl phosphate (BCIP)/nitroblue tetrazolium (NBT), BCIP/p-iodonitroblue tetrazolium (INT), BCIP alone and 3-chloro-indolyl phosphate alone. BCIP/NBT produces a purple color, BCIP/INT develops an orange pigment, BCIP yields blue, while the 3-chloro derivative provides a magenta deposit. These procedures are well known and described in Tjissen. The most vivid coloration is provided by azo dye techniques first described in the textile industry. Briefly aromatic amines such as new fuchsin are reacted with sodium nitrite forming diazonium salts. These are mixed with phosphate esters of alphanaphthol such as naphthol AS phosphate, naphthol ASBI phosphate and naphthol ASMX phosphate. Upon hydrolysis of the phosphate ester by alkaline phosphate, the diazonium compound reacts with the free alpha-naphthol forming brilliantly colored pigments. Thus, the reaction product developed with new fuchsin is scarlet, that with fast read violet LB salt, deep red, and fast blue BB salt, royal blue. Briefly, the procedure currently recommended to detect alkaline phosphatase/chitinase conjugates is as follows:

REAGENTS:
A: New Fuchsin, 4 g/dL, in 2 mol/L HCl
B: Sodium Nitrite, 5 g/dL, in water
C: Naphthol AS Phosphate, 0.75 g/L in 200 mmol/L Tris buffer, pH 8.6

PROCEDURE:
1. To 25 microliters of A, add 25 microliters of B. Mix and allow to stand 2 minutes.
2. After 2 minutes add mixture from step 1 to 10 mL of Reagent C. Mix well.
3. Add the solution from step 2 to filtered insect fragments and incubate 15 minutes.
4. Wash with water to stop reaction.
5. Place filter on glass slide, coverslip and observe microscopically. Sites of activity are scarlet.

Other aromatic amines and naphthol phosphate esters can be employed. The procedures are essentially identical.

D. FRAGMENT EXTRACTION PROCEDURE:

Ground spice stirred in an aqueous unbuffered environment forms large clumps of plant material capable of trapping many if not all insects and insect fragments. Buffering the solution offers little improvement. Addition of detergent and an antifoam agent with vigorous stirring did result in smaller clumps. A solution buffered at pH 6.2 containing tergitol and antifoam B, when subjected to controlled ultrasonic treatment, provided a uniform suspension of plant material. Similar suspensions can be obtained with heating and/or vigorous stirring without the use of detergent or sonication. Aliquots removed from this suspension and treated with magnetic bead/chitinase conjugates effectively extracted insect fragments. Some residual spice contamination was evident. The contamination varied according to whether a glass or plastic centrifuge tube was employed. Plastic tubes are preferred. Two typical procedures are outlined as follows:

REAGENTS:
A: Bis-tris/HCl buffer, 150 mmol/l, pH 6.2, or other appropriate buffers, containing 0.05% tergitol and 0.05% antifoam B.
B: Chitinase labeled magnetic beads.
C: Chitinase labeled alkaline phosphatase.

EQUIPMENT:
A. TEKMAR Model 375 sonicator/any 700 W commercial microwave
B. ROBBINS rotating mixer fitter with head to accommodate 50 mL centrifuge tubes.
C. Magnetic stir plate D. Magnetic separator E. Filter apparatus.

F. Polycarbonate filters, 47 mm diameter, 18 micrometer pore size.

G. Vacuum pump

H. Motorized micro mixer

PROCEDURE A:

1. Suspend 5.0 g of spice in 200 mL of bis-tris buffer, Reagent A. Mix thoroughly.
2. A. Place on magnetic stir plate, commence stirring and sonicate 5 minutes at 50% power; or B. Vigorously stir for 5 minutes.
3. Cool to 24°–28° C.
4. Remove a 20 mL aliquot while mixing vigorously and place in a 50 mL plastic screw cap tube.
5. Add 100 µL of chitinase/magnetic beads, Reagent B and mix on ROBBINS mixer for 2 to 15 minutes.
6. Then place tube in magnetic extractor, insert micro mixer and stir slowly for 2–3 minutes.
7. Stop stirring, allow to stand 1–3 minutes, then carefully remove all liquid by aspiration. Save this supernatant fluid.
8. Wash original tube twice with 20 mL of bis-tris buffer saving supernatants.
9. Magnetically extract supernatants discarding supernatents from these washes.
10. Add 20 mL of bis-tris buffer to original tube, mix well then transfer sequentially to remaining 3 tubes mixing well after each transfer.
11. Add 10 µL of chitinase/alkaline phosphatase, Reagent C, to the final mixture from step 10 and mix on ROBBINS mixer for 15 minutes.
12. After 15 minutes filter by suction through polycarbonate filter and wash thoroughly with 100 mL bis-tris buffer.
13. Develop color as described in previous section.
14. Enumerate manually or quantitate using the BioQuant software supplied by RM Biometrics.

PROCEDURE B:

1. Suspend 5.0 g of spice in 200 mL of bis-tris buffer, Reagent A. Mix thoroughly.
2. A. Place on magnetic stir plate, commence stirring and sonicate 5 minutes at 50% power; or B. Vigorously stir for 5 minutes.
3. Cool to 24°–28° C.
4. Remove a 20 mL aliquot while mixing vigorously and place in a 50 mL plastic screw cap tube.
5. Add 100 µL of chitinase/magnetic beads, Reagent B and mix on ROBBINS mixer for 2 to 15 minutes.
6. Then place tube in magnetic extractor, insert micro mixer and stir slowly for 2–3 minutes.
7. Stop stirring, allow to stand 1–3 minutes, then carefully remove all liquid by aspiration. Discard supernatant fluid.
8. Resuspend the magnetic beads in 10 mL of bis-tris buffer.
9. Add 10 µL of chitinase/alkaline phosphatase, Reagent C, to the final mixture from step 8 and mix on ROBBINS mixer for 15 minutes.
10. After 15 minutes filter by suction through polycarbonate filter and wash thoroughly with 100 mL bis-tris buffer.
11. Develop color as described in previous section.

Enumerate manually or quantitate using the BioQuant software supplied by RM biometrics.

Procedures A and B as outlined above do not include a sieving step. Thus, these procedures will give total counts of insect parts which are much higher than those obtained by conventional methods. Alternatively, step 4 may be modified to require passing a 20 mL aliquot of the suspension from step 3 through a 63 µm (253 mesh) sieve and then resuspending the fraction retained by the sieve in 20 mL of bis-tris buffer and transferring the new suspension to a 50 mL plastic screw cap tube. This modified procedure will yield total counts of insect parts which correspond to those obtained by conventional methods.

E. RESULTS WITH EXTRACTION PROCEDURE:

Ten samples containing precounted numbers of insect fragments were tested. The fragments were suspended in the buffer described in Section D. Chitinase immobilized on magnetic particles were added and the samples incubated with mixing for 30 minutes. The beads were then extracted by magnetic force and washed into tubes with buffer. The extracts along with remaining supernatents were then evaluated. The results were as follows:

| Sample | Fragments Added | Fragments Recovered | Delta | FR* |
|---|---|---|---|---|
| JP | 2 | 2 | 0 | 0 |
| KH | 10 | 13 | 3 | 0 |
| BN | 37 | 29 | −9 | 9 |
| PH | 41 (Moth Scales) | 47 | 6 | 6 |
| RG | 116 | 150 | 34 | 11 |
| MZ | 45 | 49 | 5 | 5 |
| TQ | 47 | 56 | 9 | 2 |
| RO | 63 | 55 | −8 | 5 |
| TC | 61 | 51 | 10 | 10 |
| QX | 48 | 44 | −4 | 3 |

*FR = Fragments remaining in supernatant after magnetic extraction

Plotting the data yielded a straight line (y=−8.3+1.22x). A correlation coefficient, r, of 0.96 was obtained. These results provide evidence that the present method is a highly efficient procedure for separating and quantitating contaminants in particulate materials.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for separating and quantitating a contaminant in a particulate material, comprising the steps:

(i) contacting the particulate material with an immobilized biomolecule which binds specifically to a contaminant to be quantitated for a time sufficient for any contaminant present in the particulate material to bind to said biomolecule, to obtain a contaminant-immobilized biomolecule complex;

(ii) separating said contaminant-immobilized biomolecule complex and any residual immobilized biomolecule from the particulate material, to obtain a separated fraction; and (iii) visually counting the amount of contaminant present in said separated fraction either by direct inspection with the naked eye or with the aid of a magnification device;

wherein said contaminant is insect parts and said immobilized biomolecule is immobilized chitinase.

2. The method of claim 1, wherein said particulate material is a food or a cosmetic.

3. The method of claim 1, wherein said particulate material is a food selected from the group consisting of flour, sugar, cocoa and ground spices.

4. The method of claim 1, wherein said particulate material is a ground spice.

5. The method of claim 1, wherein said immobilized chitinase is chitinase immobilized on a magnetic particle.

6. The method of claim 5, wherein said contacting is carried out while said food is suspended in a liquid in a reaction vessel and said separating is carried out by applying an external magnetic field of sufficient strength and for sufficient time to cause said magnetic particle to adhere to a portion of said reaction vessel and then removing said liquid suspension from said reaction vessel.

7. The method according to claim 1, wherein the visual counting of contaminant is enhanced by incubation of the contaminant-immobilized biomolecule with a biomolecule that specifically binds to said contaminant that is covalently linked to a chromophore, dye, fluorophore, or an enzyme capable of producing a detectable signal with a substrate.

8. The method according to claim 1, wherein the visual counting of contaminant is performed by an automated counting means.

9. Chitinase immobilized on a support, wherein said support is magnetic and said support is an acrolein activated bead.

10. A kit useful for the detection of a contaminant in a particulate material, comprising:

(a) a carrier being compartmentalized to receive one or more container means in close confinement therein; and (b) a first container means comprising an immobilized bimolecule which binds specifically to a contaminant to be detected, wherein said bimolecule is chitinase and said chitinase is immobilized on a magnetic support which is an acrolein activated bead.

11. The kit of claim 10, wherein said carrier is compartmentalized to receive two or more container means in close confinement therein, and further comprises:

(d) a second container means comprising a biomolecule which specifically binds to said contaminant and which is labeled with a fluorophore, chromogen or an enzyme capable of producing a detectable signal with a substrate.

12. The kit of claim 11, wherein said carrier is compartmentalized to receive three or more container means in close confinement therein, and further comprises:

(e) a third container means comprising a calibration sample comprising a predetermined amount of said contaminant.

* * * * *